(12) United States Patent
Maack (10) Patent No.: US 11,039,807 B2
(45) Date of Patent: Jun. 22, 2021

(54) SYSTEM AND METHOD FOR DARK-FIELD-IMAGING

(71) Applicant: KONINKLIJKE PHILIPS N.V., Eindhoven (NL)

(72) Inventor: Hanns-Ingo Maack, Norderstedt (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 83 days.

(21) Appl. No.: 16/470,997

(22) PCT Filed: Dec. 14, 2017

(86) PCT No.: PCT/EP2017/082734
§ 371 (c)(1),
(2) Date: Jun. 19, 2019

(87) PCT Pub. No.: WO2018/114553
PCT Pub. Date: Jun. 28, 2018

(65) Prior Publication Data
US 2020/0022668 A1    Jan. 23, 2020

(30) Foreign Application Priority Data
Dec. 19, 2016    (EP) ..................... 16205068

(51) Int. Cl.
G06T 5/50       (2006.01)
A61B 6/00       (2006.01)
G06T 5/00       (2006.01)

(52) U.S. Cl.
CPC ............ *A61B 6/5282* (2013.01); *A61B 6/484* (2013.01); *A61B 6/50* (2013.01); *A61B 6/505* (2013.01); *A61B 6/5235* (2013.01); *G06T 5/008* (2013.01); *G06T 5/50* (2013.01); *G06T 2207/10116* (2013.01); *G06T 2207/20092* (2013.01);
(Continued)

(58) Field of Classification Search
CPC combination set(s) only.
See application file for complete search history.

(56) References Cited

U.S. PATENT DOCUMENTS 5,428,657 A * 6/1995 Papanicolopoulos ........................
G01N 23/20083
378/86
2005/0122508 A1* 6/2005 Uto ........................ H01J 37/226
356/237.2
(Continued)

FOREIGN PATENT DOCUMENTS

WO    WO2016177588 A1    11/2016

OTHER PUBLICATIONS

PCT International Search Report, International application No. PCT/EP2017/082734, dated Mar. 16, 2018.
(Continued)

*Primary Examiner* — Omar S Ismail
(74) *Attorney, Agent, or Firm* — Larry Liberchuk (57) ABSTRACT

An image processing system (IPS) and a related method. The system comprises an input interface (IN) for receiving two or more input images that include respectively an attenuation signal of an imaged object and a dark-field signal of the object. A combiner (COM) is configured to combine the two or more input images in a linear combination operation to form a combined image. An output (OUT) port configured to output the combined image.

11 Claims, 7 Drawing Sheets

(52) U.S. Cl.
CPC ............... *G06T 2207/20212* (2013.01); *G06T 2207/30008* (2013.01); *G06T 2207/30061* (2013.01)

(56) References Cited

U.S. PATENT DOCUMENTS

| | | | | |
|---|---|---|---|---|
| 2006/0109949 | A1* | 5/2006 | Tkaczyk | A61B 6/032 378/4 |
| 2006/0237652 | A1* | 10/2006 | Kimchy | G06T 5/50 250/363.02 |
| 2012/0257810 | A1* | 10/2012 | Von Berg | A61B 6/5258 382/132 |
| 2015/0131777 | A1* | 5/2015 | Makifuchi | A61B 6/463 378/36 |
| 2015/0178905 | A1* | 6/2015 | Fletcher | G06K 9/4604 382/132 |
| 2017/0301066 | A1* | 10/2017 | Wang | G06T 11/008 |
| 2017/0301095 | A1* | 10/2017 | Zhang | G06T 7/12 |
| 2017/0319149 | A1* | 11/2017 | Koehler | A61B 6/4035 |
| 2018/0115705 | A1* | 4/2018 | Olsson | G06T 5/50 |

OTHER PUBLICATIONS

Yashiro W. et al., "Distribution of Unresolvable Anisotropic Microstructures Revealed in Visibility-Contrast Images Using X-Ray Talbot Interferometry", Physical Review. B, Condensed Matter and Materials Physics, vol. 84, No. 9, Sep. 1, 2011 (Sep. 1, 2011), XP055383691.

Yaroschenko A. et al., "Pulmonary Emphysema Diagnosis with a Preclinical Small-Animal X-ray Dark-Field Scatter-Contrast Scanner", Radiology, vol. 269, No. 2, pp. 427-433, Nov. 2013, http://pubs.rsna.org/doi/full/10.1148/radiol.13122413.

Skaeppler S. et al., "Signal Decomposition for X-Ray Dark-Field Imaging", MICCAI 2014, Part I, LNCS 8673, pp. 170-177, 2014.

* cited by examiner

SYSTEM AND METHOD FOR DARK-FIELD-IMAGING

FIELD OF THE INVENTION

The invention relates to a system of image processing, a method of image processing, a computer readable medium and a computer program element.

BACKGROUND OF THE INVENTION

Dark field imaging in an interferometric setup has attracted much interest especially in the medical field. However, dark field imaging experiments may still result in dark field images where signal-to-noise (SNR) ratio is lower than in an attenuation image. Experimental dark-field imaging with mice have been reported by A Yaroshenko et al in "Pulmonary Emphysema Diagnosis with a Preclinical Small-Animal X-ray Dark-Field Scatter-Contrast Scanner", *Radiology*, vol 269, No 2, November 2013.

SUMMARY OF THE INVENTION

There may therefore be a need to improve image quality, in particular in dark field imaging.
The object of the present invention is solved by the subject matter of the independent claims where further embodiments are incorporated in the dependent claims. It should be noted that the following described aspect of the invention equally applies to the image processing method, to the computer program element and to the computer readable medium.

According to a first aspect of the invention there is provided an image processing system, comprising:

input interface for receiving two or more input images that include respectively an attenuation signal of an imaged object and a dark-field signal of the object;

a combiner configured to combine the two or more input images in a linear combination operation to form a combined image, wherein the combination operation includes applying a weighting factor to at least one of the input images, wherein the weighting factor is configured to reduce a Compton scatter cross-talk in the input image that includes the dark-field signal or to reduce a beam hardening effect in the input image that includes the dark-field signal; and an output port configured to output the combined image.

Combining the two input images linearly allows "mixing" new and useful images of diagnostic value in particular in the medical field such as chest imaging.

This is particularly useful in chest imaging where the object comprises relatively low density material such as lung tissue in close proximity to high density material such as bone. In the proposed combined image beam hardening effect can be reduced and/or cross-talk between Compton scattering signal and the dark field signal can be reduced so as to better separate the two scatter contributions.

In one embodiment the combined images can be formed where the weighting factor is determined so as to reduce a contrast in the combined image in respect of one of the material components and to maintain or increase the contrast in respect of the at least one other material component. For instance, the weighing factor can be adjusted to that the combined image includes higher contrast for lung tissue whilst bone contrast is essentially eliminated at least in the region that corresponds to the lung tissue. Alternatively it is the lung tissue contrast that is essentially eliminated whilst the bone contrast remains or is increased.

In one embodiment, the combination operation includes taking a logarithm of the input images. Taking the algorithm allows better accommodating a range of the image values found in the images. Alternatively, the input images are already logarithmized.

In one embodiment, the system comprises a user interface, in particular a graphical user interface, for adjusting the weighting factor. The user may thus find suitable weighting factors experimentally through preferably real-time visual feedback.

In one embodiment, the system comprises a weighting factor determiner configured to determine the weighting factor by: forming an edge image for one material component of the object and varying a candidate weighting factor so as to reduce an edge contrast in the edge image based on an edge measure. The SNR in these images may also be improved this way. Apart from low contrast it has been observed by Applicant that the noise in the dark-field signal is lower than in the attenuation image. This has been observed to some extent in the mice images but even more pronounced in in-vivo dark-field imaging of pigs. There is not only quantum noise, but there is also an impact of other anatomical structures, which are not so relevant for the reading of the lungs. In this sense organic structures can be described as "anatomical noise". In particular the bones can be seen as anatomical noise when imaging for lungs and the proposed methods helps to reduce this effect, to in particular improve contrast and/or SNR in the dark-field signal. Other anatomical noise stems from air cavities outside the lungs (eg, the trachea) but situated in the vicinity of the lungs.

In one embodiment, the forming of the edge image by weighting factor determiner includes linearly fitting signals in respective neighborhoods in the two input images.

In one embodiment, the system comprises a visualizer configured to visualize the combined image on a display unit.

In one embodiment, the two images are supplied by an interferometric X-ray imaging apparatus. In particular a Lau Talbot interferometer is used that comprises one or more gratings.

In one embodiment, the at least one of the components has a porous or spongy structure and/or wherein one of the at least two components is bone and the at least one other component is lung tissue.

According to a second aspect, there is provided an image processing method, comprising the steps of:

receiving two or more input images that include, respectively, an attenuation signal image of an object and a dark-field signal image of the object;

combining the two or more input images in a linear combination operation to form a combined image, wherein the combining includes applying a weighting factor to at least one of the input images, wherein the weighting factor is configured to reduce a Compton cross-talk in the input image that includes the dark-field signal or to reduce a beam hardening effect in the input image that includes the dark-field signal; and outputting the combined image.

In one embodiment, the combining step comprises applying a weighting factor to at least one of the input images.

In one embodiment, the step of determining the weighting factor includes. forming an edge image for one material component of the object; and varying a candidate weighting factor so as to reduce an edge contrast in the edge image based on an edge measure.

In one embodiment, the image processing method comprises visualizing the combined image on a display device.

According to a third aspect there is provided a computer program element which, when being executed by a processing unit, is adapted to perform the method steps. According to a fourth aspect there is provided a computer readable medium having stored thereon the program element.

BRIEF DESCRIPTION OF THE DRAWINGS

Exemplary embodiments of the invention will now be described with reference to the following drawings wherein.

DETAILED DESCRIPTION OF EMBODIMENTS

Figure 1:
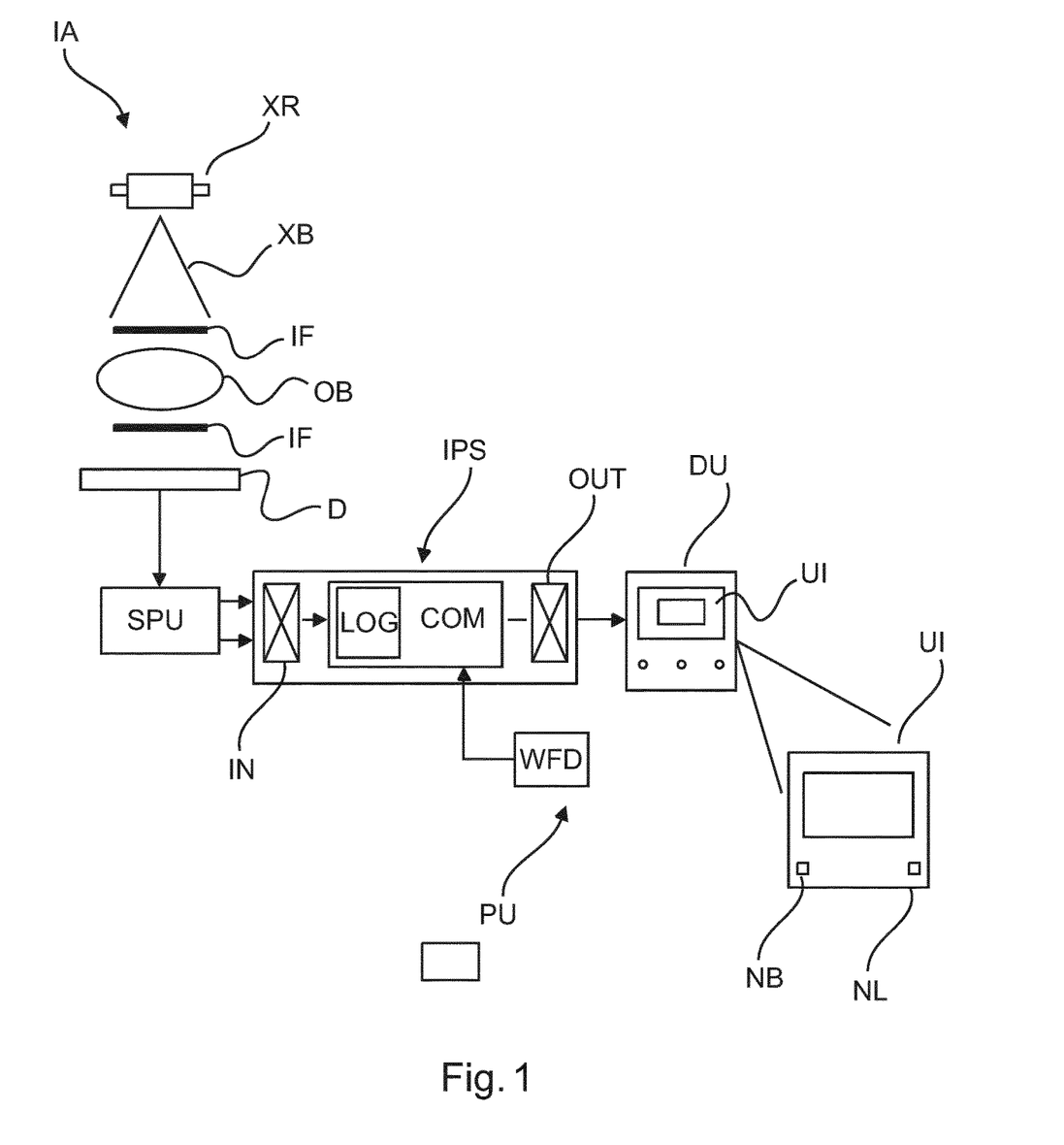
FIG. 1 shows an image processing arrangement.

With reference to FIG. 1, there is shown a schematic block diagram of an image processing arrangement that includes a computerized image processing system IPS and in one embodiment (but not necessarily all embodiments) an X-ray imaging apparatus IA.

The image processing system IPS runs on one or more processing units PU such as one or more computers, servers, etc.

Broadly, the imaging processing system IPS processes imagery produced by the imaging apparatus IA and combines the imagery in a novel way to construct a combined image which can then be displayed on a display unit DU or can be stored in a memory for later review, or can be otherwise further processed.

More particularly, the image processing system is IPS configured to receive an attenuation image and dark field image acquired by the imager IA of an object OB. The dark field image and the attenuation image are combined into the combined image. In the combined image one of at least two material components of the object OB are displayed in better contrast than the other component. It is envisaged herein in one embodiment, that the user can selectively combine the input images in different combinations with a different weighting factor so as to emphasize contrast of one component or the other. For the sake of definiteness, the image processing is particularly envisaged for medical imaging, in particular chest imaging. The object OB is for instance a chest of a human or animal (eg, mammal) patient. The proposed imaging system has been found to be of particular relevance where one of the components has a spongy or porous structure with air enclosures such as lung tissue. The image processing system may also be used with benefit for other tissue components and in fact may be used in non-medical contexts as well, where imaging of porous components embedded in at least partly non-porous components is of interest.

In the medical context mainly envisaged herein, the two components comprise in particular lung tissue and surrounding bone tissue. In one embodiment then the combined image in a first variant is so configured to encode either the bone contrast at high contrast at the exclusion of or substantially decreased lung contrast, or, in a second variant, the combined image encodes the lung contrast at high contrast but now at the exclusion of or substantially decreased bone contrast. The first variant of the combined image may be referred to herein as the "no lung image" (NL) whilst the second variant may be referred to herein as the "no bone image" (NB). More specifically, the image is "no bone" in the sense that bone contrast in front of or behind the lung (relative to the X-ray beam propagation) is reduced or eliminated.

Although in FIG. 1 it is envisaged that the imaging apparatus IA supplies direct via wireless or a wired connection the imagery to the image processing system IPS, this may not be so in all embodiments. For instance, the imagery may be first stored in a memory such as a PACS of a HIS or otherwise and the imagery to be processed is retrieved at a later stage (eg upon user request) by the IPS and is then processed.

It is envisaged in particular herein to combine the dark field image and the attenuation image in a linear combination. Weighting factors are applied to one or both of the images (in particular to only one of them) to so build the combined image. If the weighting factor is suitably adjusted, one can then generate for instance the NB image or the NL, respectively as desired. Again, in the following we will explain the invention with reference to chest imaging but this shall not exclude other applications and should not be construed as necessarily limiting what is described herein.

The combined imagery obtainable by the image processing system IPS has the further benefit that cross talk from the Compton scatter contribution into the dark field signal can be reduced. In other words, in the combined image a better separation between Compton scatter and Raleigh scatter can be achieved. Also it has been found that the effect of beam hardening on the dark field signal can also be reduced. This effect is of particular relevance here because the low density lung structure is surrounded high density bone of the rib cage. The linearly combined image may be of additional diagnostic value to users (such as clinicians) because the different tissue types (either bone or lung) are shown at more contrast compared to their respective surrounding. We suspect that both effects, Compton scatter and beam hardening, act together to cause the unexpectedly poor lung contrast in the dark-field signal when imaging in-vivo.

The input imagery (the dark field image and the attenuation image) is supplied preferably by an interferometric imaging apparatus AI. However, other, non-interferometric imaging systems may also be used instead that are capable of producing the two signals.

In a preferred embodiment the imaging apparatus AI includes an X-ray source XR and an X-radiation sensitive detector D. The imager IA can be 2D or 3D (such as a CT scanner). Between the X-ray source XR and the detector D there is defined an imaging region where the object OB (eg, the chest of the subject) to be imaged resides during imaging. In the imaging region there is also arranged an interferometer IF that includes a single, two or more grating structures. Periodicity, aspect ratio, etc of the gratings are such that they cause diffraction of the X-ray beam. Absorption and phase gratings may be used. In one embodiment the gratings are formed by photolithography or cutting in silicon wafers to define a periodic pattern of trenches. Interspaces between the trenches may be filled with lead or gold for the absorption gratings. Instead of such gratings, crystal structures may be used.

In one embodiment, an additional grating structure is arranged between the detector d and the object OB whilst the other grating is arranged between the object OB and the X-ray source X. In some embodiments there is also an additional grating arranged at the X-ray source, in case the X-ray source is incapable of generating natively coherent radiation. If the X-ray source produces incoherent radiation (which is usually the case), the (absorption) grating at the X-ray source (also referred to as the source grating) transforms the X-radiation coming out of the X-ray source into at an at least partially coherent radiation beam XB.

The at least partly coherent radiation beam XB propagates through the imaging region and interacts with the interferometer and the object OB. After said interaction, the radiation is then detected at the detector D. Generally, when X-radiation interacts with material, it experiences both, attenuation and refraction. The attenuation on the other hand can be broken down into attenuation that stems from photoelectric absorption and attenuation that comes from scatter. The scatter contribution in turn can be decomposed into Compton scattering and Raleigh scattering. For present purposes it is the Raleigh scattering (or sometimes called small angle scattering) that is of interest. It is the amount of Raleigh scattering that is modulated in the dark-field signal.

The attenuation can be understood as $I=I_0*e^{-\mu_L*h\_lungs}$, with $\mu_L$ the absorption constant of lung tissue, and with h_lungs being the in-tissue path length through the lung. The attenuation signal as recorded in the attenuation image is then $T=I/I_0$, with $I_0$ being the initial intensity before entering the lung tissue and I the intensity actually recorded at detector D.

The dark field contribution can be modelled as the visibility $V=V_0*e^{-\epsilon_L*z}$, with $\epsilon_L$ a diffusion constant for lung tissue, z=h_lungs the in-tissue path length as above, and $V_0$ being the visibility without lung tissue interaction. The dark-field signal as recorded in the dark-field image is then $D=V/V_0$.

Traditional radiography systems are usually incapable of resolving the detected signal into refraction and dark field contribution. But by using the interferometer as shown in FIG. 1 it is possible to translate these contributions into an intensity pattern of fringes which can be analyzed by signal processing system SPU. The SPU computationally splits up the detected fringe pattern at the detector into three contributions or signals, namely the refraction contribution (also referred to as the phase contrast signal), the dark field signal component and a remaining attenuation component. Ideally, there should be a clear separation of the Raleigh scatter in the dark-field signal from Compton scattering and absorption as captured in the attenuation channel.

The signal processing of the detected intensities at the detector into the three signal channels (phase contrast, dark field and attenuation) has been covered elsewhere such as by F Pfeiffer et al in "Hard-X-ray dark-field imaging using a grating interferometer", *Nature Materials* 7, pp 134-137 (2008). In Pfeiffer et al and other similar techniques as envisaged herein in some embodiment, a Fourier technique is used to analyze the fringe pattern detected at the detector D. More particularly, in one embodiment a sinusoidal signal model is fitted to the fringe pattern whilst motion is induced between the X-ray beam XB and the interferometer and/or the object. For instance, the analyzer grating (that is, the grating arranged between object and detector) is moved ("scanned") laterally relative to an optical axis of the X-ray beam. This motion causes a change of the fringe pattern which in turn can be recorded in a corresponding series for each step of the motion ("phase stepping"). This series of measurements can then be analyzed, for instance by fitting the measurements to a sinusoidal model as described in Pfeiffer et al. There are three or more parameters included in the sinusoidal model that represent, respectively, the three contributions phase contrast, dark field signal and attenuation. The phase contrast signal although sometimes of interest in its own right will be disregarded herein and it is only the dark field signal component and the attenuation component that are both forwarded to the proposed image processing system IPS. Although grating based X-ray imaging is preferred herein, other, non-grating techniques capable of providing a dark-field signal and an attenuation signal are also envisaged herein.

The dark field signals and the attenuation signals in the two channels are arranged as an ordered set of numbers, eg in respective arrays of image values. These image values or pixel values represent respectively the contrast for the dark field signal and the attenuation respectively as sensed at a respective location of the detector plane. More particularly, at a certain pixel position (x,y) there is associated a certain value in the dark field image and that value represents the amount of small scattering observed at the respective position x,y of the detector plane. The same pixel position x,y in the attenuation image on the other hand represents the amount of attenuation experienced due to Compton scatter (and photo-electric absorption). In other words, the two images have in general the same size and are naturally registered onto each other so that the respective pixel positions each represent the two physical phenomena, Raleigh scatter and attenuation (due to Compton scatter and absorption) in the two images.

As briefly mentioned earlier, it has been observed that in ex-vivo images acquired from mice, the dark field signal contrast is low and/or the SNR is occasionally unsatisfactory compared to the associated attenuation signal. Specifically, in chest imaging of pigs the lung was nearly invisible although the lung being a porous structure should have shown more contrast in the dark field image signal. It is suspected herein that the low contrast is due to cross talk from the Compton scattering into the dark-field signal. In other words, it appears that the Compton scattering is not correctly separated from the Raleigh scattering. In addition, or as an alternative explanation, the surprisingly low contrast may also be due to beam hardening caused by the surrounding tissue such as the bones and other fat/muscle tissue in which the lung is embedded. It is proposed herein and as briefly mentioned above to process the two images into the combined image, where at the least the contrast for the lung is improved at the expense of the bones or, selectively, it is the bone contrast that is improved compare to the lung contrast. It has been observed by Applicant that with the proposed method, the lung contrast is substantially eliminated in the NL images with the bone contrast remaining (or at least increasing) whilst in the NB it is the bone contrast that is substantially eliminated whilst the lung contrast remains or is even increased. Also, SNR in particular in the NB image was improved compared to the attenuation image.

In order to form the combined image, the image processing system includes a combiner COM that functions preferably as a log-combiner with a logarithmizer stage LOG. Any logarithmic base, such as 10 or ($e\approx2.72\ldots$) may be used.

In more detail the input imagery, the dark field image D and attenuation image T, are received at input port IN of the signal processing system SPS. The two images are then pixel-wisely combined in the combined COM by forming a log-linear combination of the two image values (dark field and attenuation) at each pixel position respectively. The log-linear combination can be formed in different ways. In the preferred embodiment, the received input images are first passed through the logarithmizer LOG stage to pixelwise form respective log images, referred to herein as Log(T) and Log(D). The combined image C is then formed pixelwise as a linear combination at an arithmetic stage of the combiner stage COM from the respective log-image values in the log-input imagery log(T), log(D) at respective image positions x,y (pixel for 2D or voxel for 3D or higher dimensions, all envisaged herein):

$$C(x,y)=\lambda*\log(T)(x,y)+/-\mu*\log(D)(x,y) \quad (1)$$

Weighing factors $\lambda$, $\mu$ are then used to achieve the no bone image or the no lung image.

Ansatz (1) can be simplified by through-multiplication to formulate (1) using only as single weighting factor, for instance:

$$C(x,y)=\log(T)(x,y)+/-w*\log(D)(x,y) \quad (2)$$

Alternatively, eq (1) can be reformulated so the weighting factor in eq (2) is only applied to the attenuation image log(T). In the following we will use the formulation (2) without excluding the other embodiments, namely (1) or where w is applied only to log(T). The weighing factor w has been found experimentally to be somewhere between 1 and 10, but this of course the exact magnitude depends how exactly the image values are encoded (that is, the mapping onto a grey or color value palette, etc.). In one embodiment as per (2), the absolute value of the weighting factor is larger than unity $|w|>1$ or at least $|w|>0.5$, eg 0.8. The weighing factor can be positive or negative, so the combination operation of COM is effectively either an addition or subtraction. For the NL image, $3<w<4$, in particular w=3.4 in one embodiment for mice or pig images. For The NB image, $0.5<w<15$ has been observed by Applicant. However the exact boundary range for NL and NB depends on the condition of the lung, and on the sensitivity of the interferometer IF, etc.

Conceptually, the requirement $|w|>1$ can be understood as follows: because there appears to be a cross-talk contribution from Compton into the dark-field signal, we need to increase the weight for the dark-field signal relative the attenuation signal. Alternatively however, if the weighting factor is applied only to the attenuation term instead of the dark-field term, then the weighting factor is $|w|<1$ to decrease the attenuation channel relative to the dark-field channel. In this sense, the proposed method may also be understood as a Compton correction method.

In other words, $|w|$ is a measure for the ratio between the relative strength between the dark field signal and the attenuation signal. For healthy lungs the magnitude $|w|$ is larger than for emphysematous lungs (which are of spongier consistency than healthy lungs). The magnitude $|w|$ may also be displayed alongside the combined image C as a measure for a stage of a lung condition. What has also been found is that $|w|$ is about 4 times larger in ex-vivo lung imaging (where lung tissue is suspended in a liquid such as water in a receptacle) than in in-vivo imaging.

In addition, the proposed method also functions to reduce beam hardening artefacts in the dark-field signal. In particular unwanted contrast of bones in the dark-field image can be reduced.

The weighting factor for beam hardening and Compton correction is the in general the same. The magnitude appears to depend on the attenuation factor of bone in the relevant X-ray spectrum. In other words, one can always find a specific w(kV) which depends on the tube XR voltage kV. The factors can be thus pre-computed for each kV or kV range and the respective factor w(kV) can then be used for different kVs as per required by the imaging protocol.

It is also envisaged herein that the weighing factor can be changed by the user, preferably interactively by a graphic interface UI. For instance, the combined image C for a given weight in the log-linear combination is rendered by a visualizer VIS in a pane of a window widget of the graphic interface UI. An exemplary embodiment of the graphical UI is shown schematically in inset FIG. 1A. A slider widget (not shown) or one or more push button widgets NL,NB allow the user to change the weighing factor either continuously or in steps, respectively, to generate the change in contrast of the resulting combined image. The combined image is preferably rendered in real time with the user changing or adjusting the weighing factor. In one embodiment as shown in FIG. 1, the user interface UI comprises two different buttons NL and NB and the user can switch or "toggle" between the no-lung NL image and the no-bone NB image by selectively operating a corresponding one of the buttons NL, NB. The push button widgets or the slider widget can be operated by touch screen action or with a pointer tool such as a stylus or computer mouse. User interfaces UI other than graphical are also envisaged where the user specifies the weighting factor in a textbox and dispatches same by keystroke, or other non-graphical input means.

As mentioned above, the weighting factor w for the linear combination can be determined experimentally and can be changed by the user or may be computed automatically by a weight factor determiner WFD. Operation of this will be explained in more detail below at FIG. 2 to which reference now made.

Figure 2:
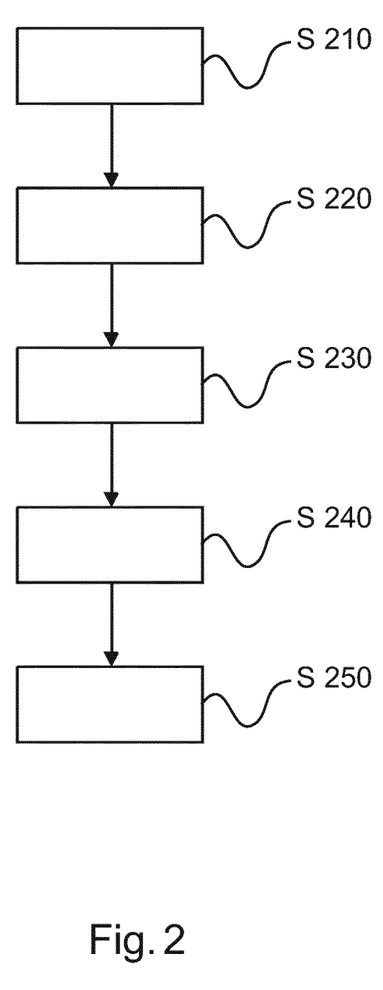
FIG. 2 shows an image processing method.

Specifically, FIG. 2 shows a flow chart of a proposed image processing method that underlies operation of the image processing system IPS of FIG. 1. It will be understood however, that the method steps described in the following constitute a teaching in their own right and are not necessarily tied to the specific architecture shown in FIG. 1.

At step S210 the dark field image and the attenuation image are received, not necessarily at the same time. The imagery can be supplied direct from an imager AI, in particular an interferometric imager, or it may be retrieved from an image storage/memory/database such as the PACS, or other.

The dark field image and the attenuation image have been acquired of the same object, in particular a multi-component object such as the mammal chest including bone and lung tissue.

At least some of the components such as the lung include small air enclosures and/or has a porous structure. It is then expected that the porous structure in particular will show at high contrast in the dark field image which however is not always the case because of bogus cross-talk contributions from Compton scattering or beam hardening effects. The proposed method allows improving contrast in at least the dark field image so as to better separate the dark field signal from the Compton scatter signal.

To achieve this better separation, a linear combination is formed at step S230 from the two input images as per eq (1), (2) or their variants as discussed above. Although in principle two factors $\mu,\lambda$ can be used as in (1), one for attenuation image and one for the dark field image, it is computationally more efficient to merely apply the weighing factor to one of the two images, for instance only to the dark field image as in (2) or only to the attention image (not shown here). The weighing factor w is either determined experimentally or it can be determined automatically at step S220. Step 220 will be explained in more detail below at FIGS. 3-5.

The combination operation at step S230 is in particular a log-linear combination. In particular, first the logarithms are formed from each of the two input images and the so obtained log images are then combined as per eqs (1), (2). Where logs are taken first, the weighting factor is then applied to log(T) or log(D) or both, and then subtraction or addition is performed.

Alternatively, however, taking advantage of the logarithm laws, exponentiation and multiplication operation can be used instead:

$$C(x,y)=\log [T(x,y)*D(x,y)^w] \qquad (3)$$

In this embodiment the two input images are first point-wisely multiplied to obtain a product image. It is then this product image from which the logarithm is then taken. The application of the weighing factor can be achieved by point-wise raising the dark field or the attenuation image or both to respective powers w. Preferably, however, the logs are taken first and the log images are then added/subtracted as per (1), (2). Whether or not eqs (1), (2) or (3) is used, we will any case refer to w as the weighing "factor".

It will also be appreciated that depending on the image value encoding (HU or other unit), the weighting factor may either be positive or negative so that the combination operation in eq (1-3) is either an addition or a subtraction.

At step S240 the combined image is then output, for instance committed to memory and/or visualized in step S250 on the display device of a portable or stationery device such as a tablet/smart phone/laptop or work station, respectively. Preferably, the combined image C is displayed on a workstation associated with the imager IA.

Preferably, the method is used in real time as the images are supplied by the imager but may also be used in an offline environment where the images are reviewed after retrieval from database or other memory.

As mentioned, the proposed method can be used to determine the weighting factor w in such a manner that either contrast for (only) one of the components are shown at the expense of the other material component. For instance, in chest imaging the factor w can be chosen in the combined image C so that the bone structures are shown, but not the lung structures or, alternatively, or conversely there is only lung structure contrast but no bone contrast.

In the following the step S220 of determining the weighing factor is described in more detail. The method will be described (without limitation) in the context of chest imaging to determine the weighing factor $w_{NL}$ for the no lungs image NL although it will be understood that a similar procedure can also be used for computing a weighting factor $w_{NB}$ for no bones image NB.

The basic rationale is as follows. If the combined image is a no lung image NL, there should be no contrast or edges in particular for the lung's outer contour (although there still may be bone contrast). In other words, if we form a linear combination with a candidate weighing factor w and we vary the factor w, we should be able to achieve that the lung contrast vanishes whilst the bone structures remains. If we then define an edge measure that measures a strength of the lung edges and if there is a functional relationship between this edge measure and said candidate factor w, we can vary same either manually or preferably in an optimization scheme to minimize the edge measure. Once the minimum is achieved, the associated candidate factor is output and applied in any one of eqs (1-3) to effect the combination image C.

Figure 3:
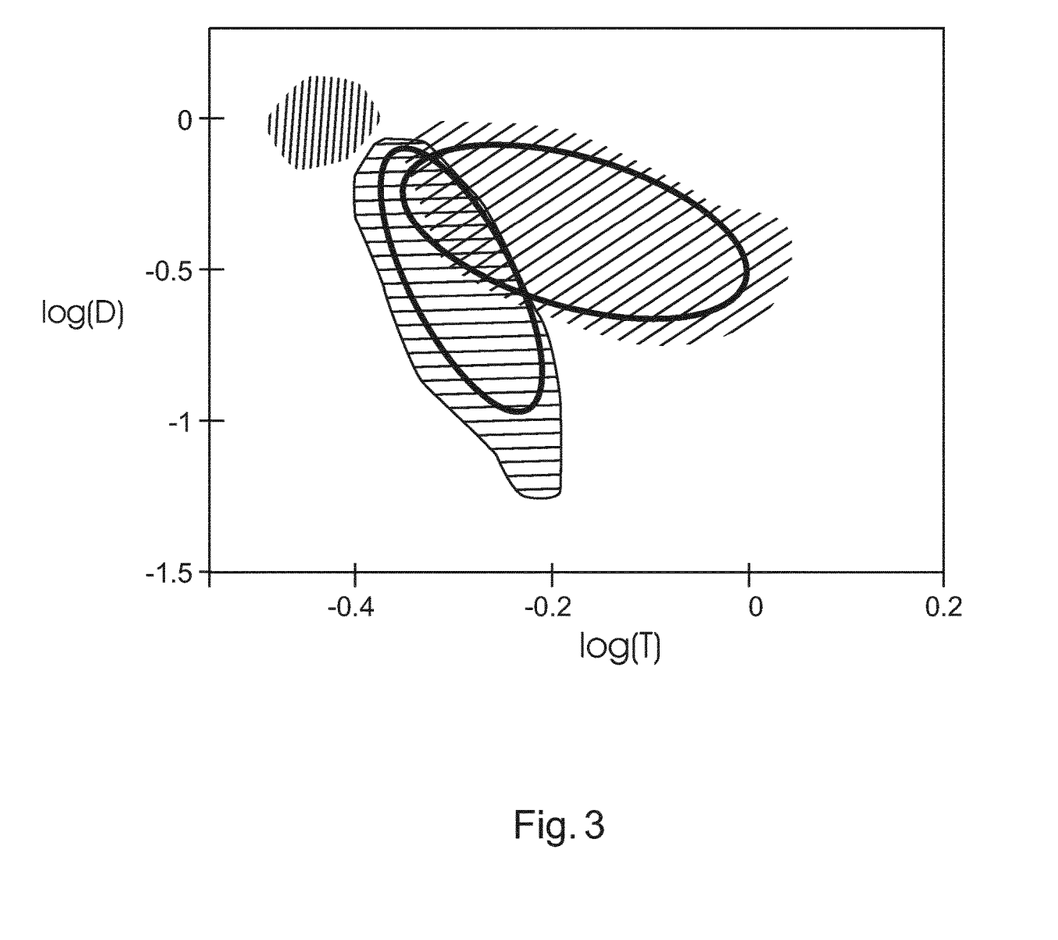
FIG. 3 shows a graph of a relationship between a dark field signal and an attenuation signal in interferometric imaging.

The graph in FIG. 3 further helps to motivate the proposed method of determining the weighing factor. The graph shows the logs of attenuation value log(T) on the horizontal axis graphed against the log of the dark field signal log(D), shown on the vertical axis. Specifically, FIG. 3 is a scatter plot of the lung tissue of mice from a dark field examination as reported by Yaroshenko et al cited above. The scatter plot shows three point clouds: A spherical one at the upper left hand which represents the distribution of image value pairs for background. The other two point clouds are elliptical in shape. The more slender, elongated ellipse corresponds to log(T)–log(D) image value pairs taken from healthy control lungs whilst the thicker ellipse is formed from values taken from emphysematous lungs. Emphysematous lungs are "more spongy" and hence cause a weaker dark field signal because of larger air cavities as compared to healthy lung tissue. In other words, when imaging unhealthy lungs, Compton scatter or beam hardening induces lower contrast and/or lower SNR we have a weaker linear correlation (that is, the slope of the ellipse's major axis is closer to zero) between dark field and attenuation. In light of this, Applicant proposes to perform a linear fitting to the local distribution of dark field and attenuation values. The slope of the respective linear curve of the fitting line has then been found by Applicant to correspond to the desired weighing factor $w_{NL}$ for the no lungs image. We can use the slope of the lines as a measure for the dark-field signal strength.

Figure 4:
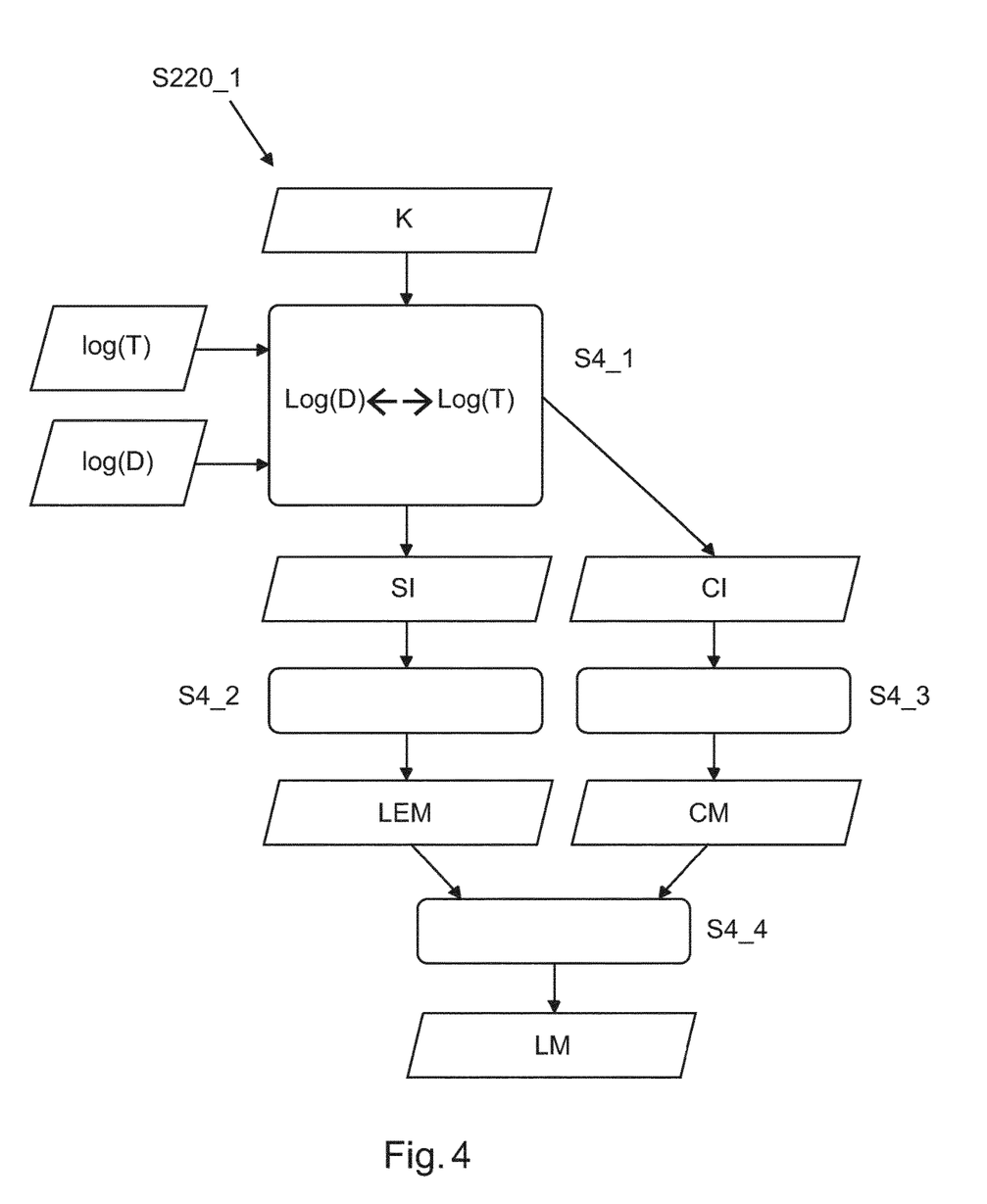
FIG. 4 shows a method step in the method of FIG. 2 for forming an edge image.
Figure 5:
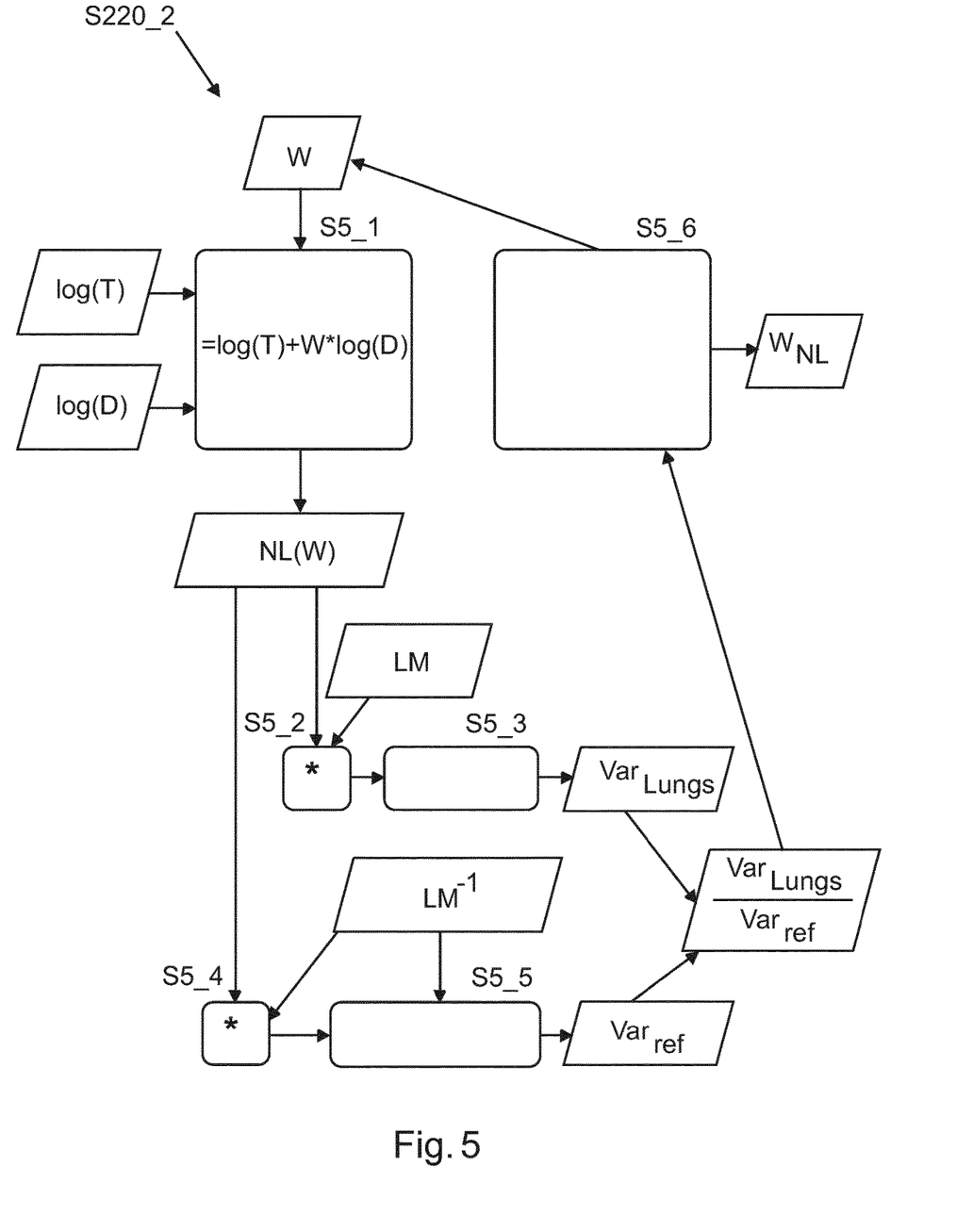
FIG. 5 shows a method step in the method of FIG. 2 for defining an edge measure.

Reference is now made to FIGS. 4 and 5 where the weighting factor determining step S220 (according to one embodiment) is described in more detail. The approach is inspired by the observations above in relation to FIG. 3.

The steps are broadly as follows. In step S220_1 an edge image is formed for the material component of interest (in this case the lung). In the edge image we wish to diminish or remove completely the unwanted lung contrast.

Once the edge image has been formed, a (candidate) weighing factor of the estimate is then varied in step S220_2 so as to reduce the contrast as per the edge measure. Once the minimum of the edge measure has been found, then the current candidate weighing factor corresponds to the desired weighing factor and this is then output and applied to the combined image to so build the no lungs image.

Turning now first to step S220_1 in more detail with reference to FIG. 4, in step S4_1 a localized linear fitting for small neighborhoods in the two input images Log T and Log D is performed. This can be done by defining a kernel size K (such as for instance K equals 7 pixels which then defines a neighborhood of 7×7=49 pixels). The kernel shape may be rectangular (not necessarily square) or round.

Kernel K is then being slid successively over the respective images log(T), log(D) to extract respective image values. These Log(T) and Log(D) image values then form pairs in a localized scatter plot. A linear fit according to known methods is then performed for the neighborhood K at the respective kernel position and the slope of the respective fitting line is then recorded for the respective kernel location in a "slope" image SI.

At step S4_2 the slope image is then thresholded to arrive at a lung map LEM. Optionally, or instead of forming a slope image, a correlation co-efficient is computed in each kernel window K to form a correlation image CI. Image CI can then again be thresholded to arrive at a correlation map CM.

The required edge map LM is then output as step S4_4 as either the LEM map or the CM map.

Alternatively, the two maps LEM and CM can be combined by selecting only those values from C and LEM where both lie above a common threshold. In other words, a logical AND operation is performed point-wise to the two images CM and LEM to so build the edge image LM.

In any of these embodiments, the edge image (referred to herein as lung map in the chest imaging context) may be represented as a bitmap (or "mask") having an entry at a certain pixel position if only if the respective image value is above the single or common threshold. This lung map is one embodiment of the edge image as explained above but the method step S220_1 can be applied to other tissue types or outside medical contexts.

The edge image (lung map) is then used in step S220_2 to then find the optimal weighting factor $w_{NL}$ for the no lung image NL. This is now explained in more detail in FIG. 5.

In step S5_1, an initial guess for the weighting factor W is used to form a linear combination (as per any of eqs 1-3 or their variants) of the dark field image Log D and the attenuation image Log T. This linear combination with W is the estimate NL(W) for C. The lung map LM as formed in FIG. 4 is then used to localize locations of an edge in the estimate image NL(W).

An edge measure is then applied at step S5_3 to measure a strength of the edges at the respective locations as per the lung map LM. In one embodiment this can be done by computing the statistical variance or by computing the gradients or otherwise. The statistical variance is computed in a neighborhood around an edge point as per map LM.

The edge measure ("var_lungs") is then output. An optimization scheme can now be used at step S5-6 such as Newton-Raphson or Conjugate Gradients, etc to vary the initial guess W to so find the correct weighting factor $w_{NL}$ where the edge measure as output at step S5_3 is a minimum or falls under a preset optimization threshold.

In one embodiment, the lung map is additionally inverted at optional S5_5 step and it is also the variance in the inverted lung map that is computed analogous to step S5_3. The inversion is achieved by mapping 1's to 0 and 0's to 1's. A ratio is then formed from the two variances as per steps S5_3, S5_5 and it is this ratio that is then used as the edge measure which is to be optimized. The forming of the ratio constitutes a normalization of the variances to form a normalized edge measure which is more robust. It will be appreciated that the normalization may also be used for quantities other than variances (eg, gradients, etc).

The above described procedures in FIGS. 3, 4 and 5 can also be applied to find the no-bones NB image. In this case, a bone map is created in the above steps. In other words, the proposed method provides an alternative to known bone suppression algorithms.

In sum, the "no bones" NB or "no lung" image NL are constructed as respective linear combinations in order to reduce the effects of beam hardening and cross-talk of Compton scatter into dark field signal to better separate the two scattering types.

It will be understood that in step S220_2, it is in principle sufficient to evaluate a single edge location as per the edge map and to optimize for W at this location only. Alternatively, multiple locations on the edge map can be selected, and one optimizes for W at each location separately and then forms an average to arrive at the correct factor. The single or the multiple locations in the edge image may be selected at random or by the user whilst the edge map is displayed.

In yet other embodiments, the optimization may be run in an additional loop over all points along the edge map (at a suitable step-width) and one optimizes over the entire edge image.

Figure 6:
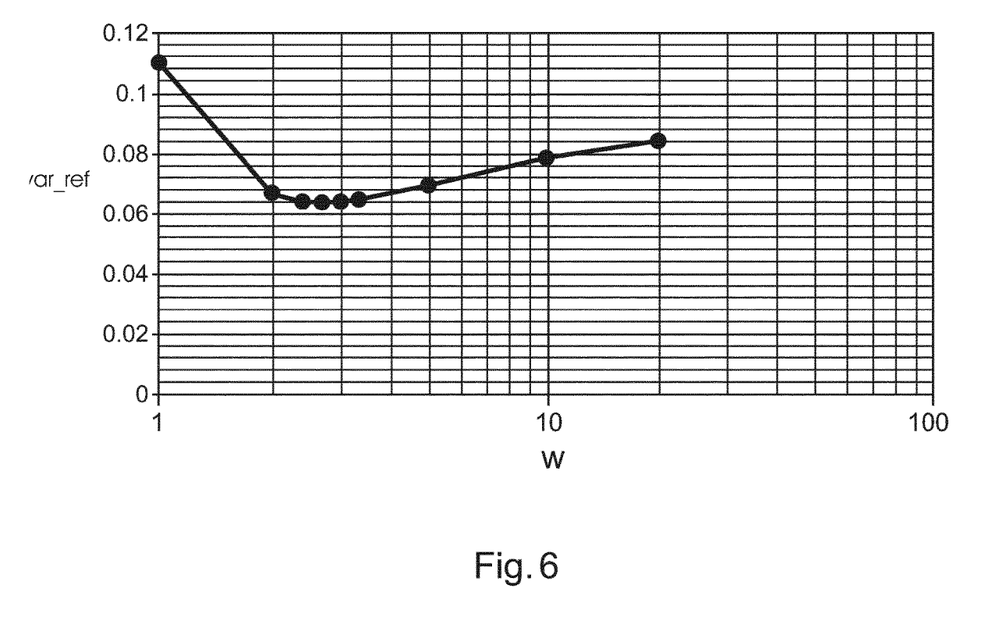
FIG. 6 shows a diagram where an edge measure is graphed against a weighing factor.

FIG. 6 shows an example from a test run of the method step as per FIGS. 4,5. In the diagram, weighing factor W (along the horizontal axis) is graphed versus the variance ratio (along the vertical axis) as described above. In this case the minimum of the edge measure W is attained at about W=8.

The approach in FIGS. 4,5 is merely one embodiment which is not to exclude others. For instance, in an alternative embodiment, step S220_1 may instead be implemented by a parameterized segmentation scheme. The parameter represents the local edge strength in the segmentation and this is then optimized so that the edge strength is minimal (or falls below a certain threshold) to so find the optimal weighting for the linearly combined image C.

Figure 7:
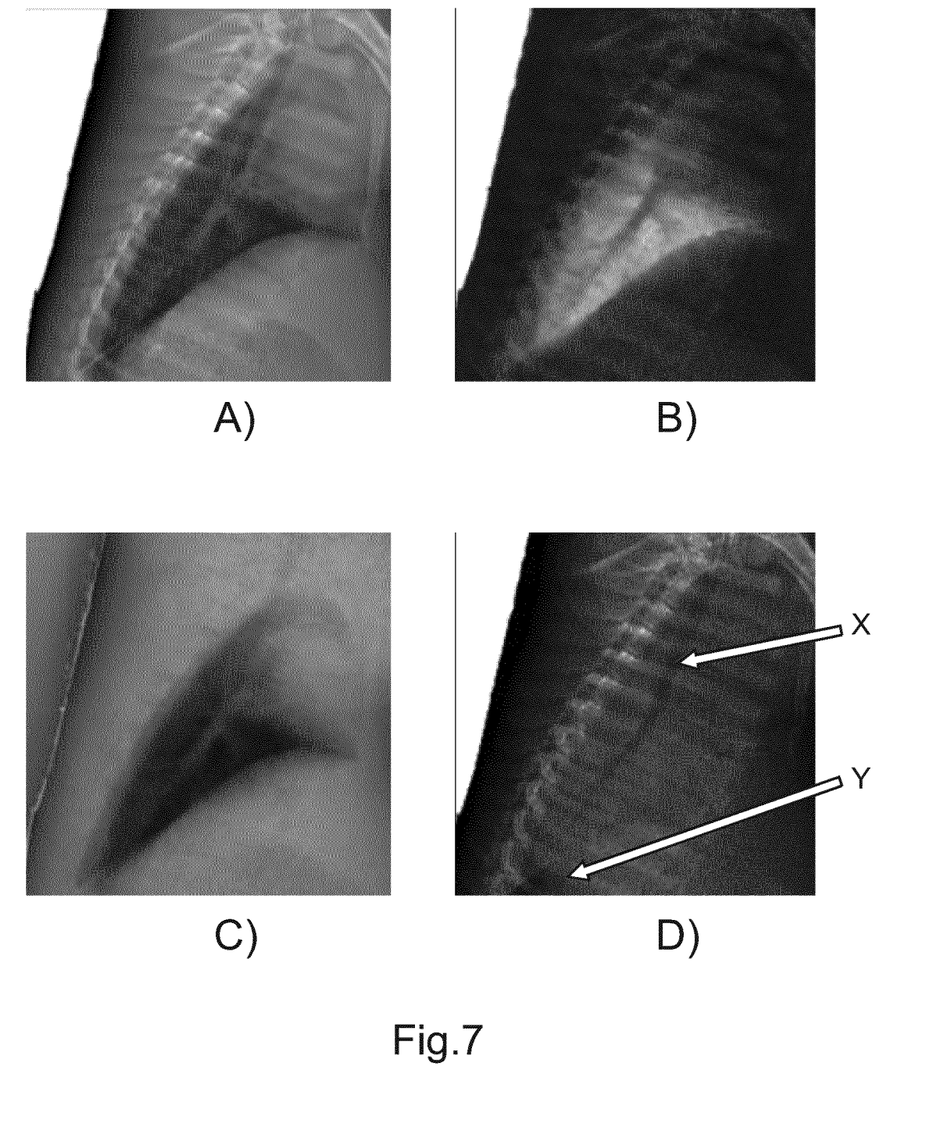
FIG. 7 shows imagery obtainable with the proposed method in comparison with unprocessed imagery.

FIG. 7 shows exemplary imagery obtained from pigs to illustrate the benefits of the proposed method. Specifically, FIG. 7 shows in-vivo chest imaging in pigs. Image A) shows the attenuation image and B) shows the dark field image channel without the proposed processing.

As per A), the image signals in the lung region (shown as the triangular image area) stem largely from the porous lung structure. However, other air enclosures such as in the bones may cause similar signals. In other words, the unprocessed attenuation image obtained from an interferometric X-ray apparatus shows regular tissue and lung tissue but also air cavities outside lungs. The situation is different in unprocessed dark field imagery B) where regular tissue lungs are shown but no air cavities. In other words, the signals within the lung region come entirely from the inside of the lungs but not from the lung tissue itself. The more porous structure of emphysematous lungs causes heavy Raleigh scatter which shows as contrast whilst larger air cavities cause barely any contrast.

The lower row of FIG. 7 at C), D) shows images A) B) after linear combination with the correct weighting factor w. Specifically, C) shows a lung only image with no regular (that is, non-lung tissue) contrast but only lung tissue contrast but with no air cavity contrast outside the lung. Image D) shows a bone only image which is a Compton scatter or beam hardening corrected dark field image B). Regular air cavities are shown but not the lung tissue itself. For instance, arrow X shows the trachea as an air enclosure while arrow Y points to another air cavity. This can be explained as follows: a (too) basic anatomic model of the lung would correspond to the following description: "lung tissue filled with air". But this simple model is valid only to explain how the lung looks in an attenuation image: the lungs are dark in the traditional grey value mapping scheme. But the above data in the context of the proposed in dark-field imaging asks for a more refined model to explain the imager in FIG. 7. This refined model describes the lung as including "lung tissue in which alveoli are formed which in turn are filled with air". This more detailed model explains why the lungs show up in the dark field image but other cavities do not. This is the reason why the trachea X and colon-cavity Y show up in the "no-lungs-image" D. in other words, the alveoli have the right microstructure to generate dark-field signals.

In the proposed method, by choosing a suitable weighing factor in the linear combination of the two channels (dark field and attenuation), air contrast in the combined image can be separated into air within lung tissue and air in other parts of the body outside the lung tissue (like the trachea at arrow X in Figure D above). The air cavity shows significantly more contrast and/or higher SNR (encoded as a dark structure) in D) and can be identified easier than due to the absence in the lung-only image to the left at C). In case of C),D), the w-factor was found so as to minimizes the contrast of the lungs in respect to its surrounding. As the signal in the log(T) image is negative (lung=less soft tissue) and positive in the Dark Field Image (lung=more Rayleigh scatter) the log-images are added using a positive w-factor. In the example, C), D), w was found to be about 3.4.

Image C) is a NB image whilst image D) is an NL image. Image D) also illustrates that air outside the lung (eg in the trachea) is not removed whilst the small air filled alveoli (which mainly cause the dark-field signal in this part of the mammal anatomy) are removed. As a further consequence, the trachea (although air filed) does not produce any contrast in the NB image C). In image D), the SNR is increased compared to B) or A). The image processing system IPS may be implemented as software modules or routines in a single software suit and run on a general purpose computing unit PU such as a workstation associated with the imager IA or a server computer associated with a group of imagers. Alternatively the image processing system IPS may be arranged in a distributed architecture and connected in a suitable communication network.

Alternatively some or all components of the IPS may be arranged in hardware such as a suitably programmed FPGA (field-programmable-gate-array) or as a hardwired IC chip.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium (in particular, but not necessarily, a non-transitory medium), such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An image processing system, comprising:
   an input interface configured to receive at least two input images that include an attenuation signal of an object and a dark-field signal of the object;
   a weighting factor determiner configured to determine a weighting factor by forming an edge image for one material component of the object and varying a candidate weighting factor so as to reduce an edge contrast in the edge image based on an edge measure;
   a combiner configured to combine the at least two input images in a combination operation to form a combined image, wherein the combination operation includes applying the weighting factor to at least one of the input images, wherein the weighting factor is configured to reduce a Compton scatter cross-talk in the input image that includes the dark-field signal or to reduce a beam hardening effect in the input image that includes the dark-field signal; and
   an output port configured to output the combined image.

2. The system according to claim 1, wherein the combination operation includes taking a logarithm of the input images.

3. The system according to claim 1, further comprising a user interface for adjusting the weighting factor.

4. The system according to claim 1, wherein forming the edge image by the weighting factor determiner includes linearly fitting signals in respective neighborhoods in the two input images.

5. The system according to claim 1, further comprising a visualizer configured to visualize the combined image on a display unit.

6. The system according to claim 1, wherein the at least two images are supplied by an interferometric X-ray imaging apparatus.

7. The system according to claim 1, wherein the object comprises at least two material components, wherein the weighting factor is determined so as to reduce a contrast in the combined image in respect of one of the material components and to maintain or increase the contrast in respect of the at least one other material component.

8. The system according to claim 7, wherein at least one of the components has a porous or spongy structure, and/or wherein one of the at least two components is bone and the other component is lung tissue.

9. An image processing method, comprising:
  receiving at least two input images that include an attenuation signal image of an object and a dark-field signal image of the object;
  applying a weighting factor to at least one of the input images;
  determining a weighting factor by:
    forming an edge image for one material component of the object; and
    varying a candidate weighting factor so as to reduce an edge contrast in the edge image based on an edge measure;
  combining the at least two input images in a combination operation to form a combined image by applying a weighting factor to at least one of the at least two input images, wherein the weighting factor is configured to reduce a Compton scatter cross-talk in the input image that includes the dark-field signal or to reduce a beam hardening effect in the input image that includes the dark-field signal; and
  outputting the combined image.

10. The image processing method according to claim 9, further comprising visualizing the combined image on a display device.

11. A non-transitory computer-readable medium having one or more executable instructions stored thereon, which, when executed by a processor, cause the processor to perform an image processing method, the method comprising:
  receiving at least two input images that include an attenuation signal image of an object and a dark-field signal image of the object;
  applying a weighting factor to at least one of the input images;
  determining a weighting factor by:
    forming an edge image for one material component of the object; and
    varying a candidate weighting factor so as to reduce an edge contrast in the edge image based on an edge measure;
  combining the at least two input images in a combination operation to form a combined image by applying a weighting factor to at least one of the at least two input images, wherein the weighting factor is configured to reduce a Compton scatter cross-talk in the input image that includes the dark-field signal or to reduce a beam hardening effect in the input image that includes the dark-field signal; and
  outputting the combined image.

* * * * *